United States Patent [19]

Suzuki et al.

[11] Patent Number: 5,130,555
[45] Date of Patent: Jul. 14, 1992

[54] TAPE CREASE INSPECTING METHOD AND APPARATUS HAVING A STRIPE SHAPED PATTERN REFLECTION PLATE

[75] Inventors: Noriyuki Suzuki, Neyagawa; Yoshikazu Okahashi, Ikoma; Hirofumi Fujiwara, Toyonaka; Katsunori Oka, Daitou, all of Japan

[73] Assignee: Matsushita Electric Industrial Co., Ltd., Osaka, Japan

[21] Appl. No.: 548,878

[22] PCT Filed: Nov. 28, 1989

[86] PCT No.: PCT/JP89/01199
§ 371 Date: Sep. 17, 1990
§ 102(e) Date: Sep. 17, 1990

[87] PCT Pub. No.: WO90/06505
PCT Pub. Date: Jun. 14, 1990

[30] Foreign Application Priority Data
Nov. 28, 1988 [JP] Japan .................. 63-299803

[51] Int. Cl.⁵ .............................. G01N 21/86
[52] U.S. Cl. .................... 250/559; 250/570; 356/374; 356/237
[58] Field of Search ........... 250/570, 571, 559, 237 G; 356/376, 374, 401, 237, 430

[56] References Cited

U.S. PATENT DOCUMENTS

| | | | |
|---|---|---|---|
| 4,682,041 | 7/1987 | Egami et al. | 250/571 |
| 4,794,550 | 12/1988 | Greivenkamp, Jr. | 356/376 |
| 4,802,759 | 2/1989 | Matsumoto et al. | 356/376 |
| 4,939,380 | 7/1990 | Berger et al. | 250/237 G |

Primary Examiner—David C. Nelms
Assistant Examiner—Que T. Le
Attorney, Agent, or Firm—Wenderoth, Lind & Ponack

[57] ABSTRACT

A projector and a reflection plate with stripe shaped patterns printed on it are used for projecting the reflection light of the stripe shaped pattern onto a tape. An inspection apparatus for inspecting the crease condition of the tape by analyzing the pitch of the stripe shaped pattern projected onto the tape on a plurality of inspection lines is provided so that the change condition of delicate creases may be detected in a short time.

18 Claims, 13 Drawing Sheets

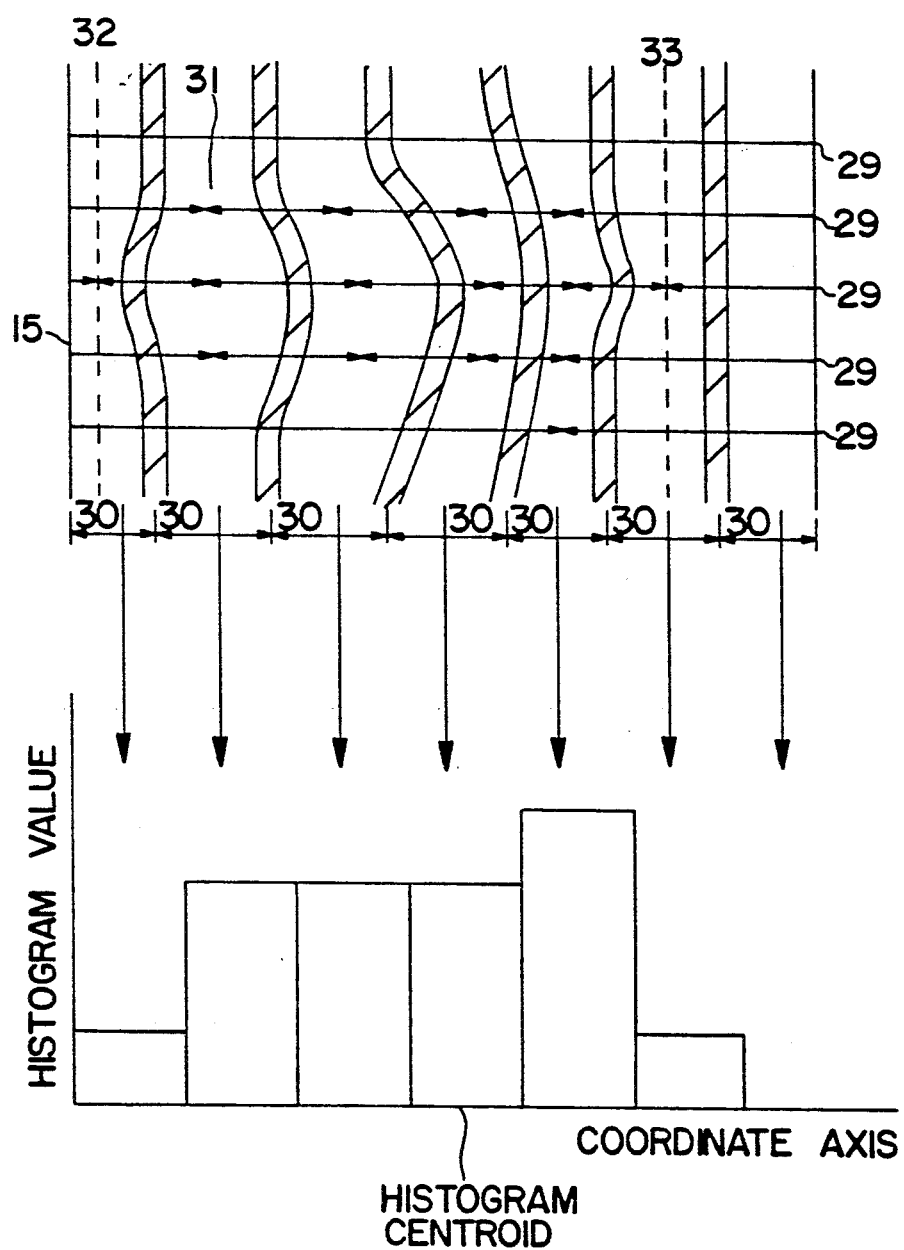

TAPE CREASE INSPECTING METHOD AND APPARATUS HAVING A STRIPE SHAPED PATTERN REFLECTION PLATE

BACKGROUND OF THE INVENTION (1) Field of the Invention

The present invention relates to a method of inspecting tape creases to be effected at a step for inspecting and adjusting the tape crease condition in the manufacturing of video decks, an apparatus therefor, and an adjusting apparatus using the method.

2. BACKGROUND ART

A conventional tape crease inspecting method, and the inspecting and adjusting apparatuses therefor, will be described with reference to the drawings.

FIG. 12 is a diagram showing the construction of crease inspecting and adjusting apparatuses using a tape crease detecting means with conventional moire stripe processing. FIG. 13 is a view showing a condition of the light projected onto the tape by a tape crease inspecting and adjusting apparatus as shown in FIG. 12.

In FIG. 12, 1 is a projector, 2 is an image pickup apparatus, 3 is a diffraction grid for causing moire stripes, 4 is tape, 5 is a picture processing apparatus, 6 is an actuator control apparatus, and 7 is an adjusting actuator for adjusting the creases of the tape.

In FIG. 13, 8 is a moire stripe projected onto the tape 4 by the diffraction grid 3. 9 is reflection light from the deck (not shown). 10 is a central line of the moire stripe 8. 11 is a straight-line approximation of the moire stripe 8. 12 is the displacement with respect to the straight-line approximation 11 of the moire stripe 8.

In FIG. 12, the light from the projector 1 passes through the diffraction grid 3, and is cast as the moire stripe onto the tape 4. The cast light is introduced by the imaged pickup apparatus 2 to effect the crease inspection of the tape 4 by the picture processing apparatus 5. A judgement standard for the creases of the tape 4 is the size of the bending of the moire stripe and the bent stripe. In FIG. 13, the size of the bending of the moire stripe is given in a maximum value in the displacement 12 with respect to the approximately straight-line 11 of the moire stripe 8. Also, the position of the bent stripe is given in the position of the displacement provided as the maximum value. In this manner, the condition of the creases is discriminated by the picture processing apparatus 5 so as to effect the inspection of the creases. When the crease of the tape 4 is not appropriate, through the results of the inspection, the actuator control apparatus 6 moves the adjustment actuator 7 so as to effect the adjustment of the creases. Thereafter, the inspection adjustment is repeated until the crease becomes appropriate in condition.

But, in the method of casting the light onto the tape 4 through such a diffraction grid 3 as shown in FIG. 12, the reflection light 9 from the deck is also cast, as shown in FIG. 13. The moire stripe 8 cast onto the tape 4 by the projector 1 is worse in contrast, with the boundary between the moire stripe 8 and the tape 4, which becomes the background, being ambiguous.

Due to the items described above, the picture pickup by the image pickup apparatus 2 is not in good condition. Also, a complicated picture processing algorithm is required to calculate the maximum displacement amount with respect to the straight-line approximation 11 of the moire stripe 8 by the picture processing apparatus 5. Accordingly, the inspection time of the crease takes about several tens of seconds in the apparatus shown in FIG. 12. This speed is not practical. Also, in order to detect the crease condition of the running tape, it is required to detect the dynamic changes in the crease of the tape. To detect it, the detection time of the crease must be short.

Further, as shown in FIG. 12, the diffraction grid 3 has to almost adhere on the tape 4, and this positioning is difficult to effect.

Further, in the discrimination of the crease, the condition changes in very small creases are complicated. The condition change is not determined by the maximum displacement amount with respect to the straight-line approximation 11 of the moire stripe 8, but only by the position thereof. Namely, the characteristic amount of many more creases is required to be extracted, and also, a plurality of characteristic amounts are required to be matched properly with respect to the condition changes in complicated creases.

Further, the condition changes in very small creases are complicated, and the quality standard of the crease condition has to, at present, depend upon human physical judgement. Namely, the discrimination result of the crease is required to correspond to the human physical judgement.

Further, as the change condition of very small creases cannot be detected properly in the apparatus shown in FIG. 12 due to the above described items, it is difficult to adjust the crease of the tape quickly and properly with the condition of the crease detected by the use of the apparatus.

SUMMARY OF THE INVENTION

Thus, in order to solve this problem, the present invention provides a tape crease inspecting method simplifying the positioning operation of the stripe pattern, inspecting the crease condition by the projection picture with the boundaries of the patterns in better contrast and being clear. The present invention also provides a tape crease inspecting apparatus which can quickly discriminate the condition changes in complicated and very small creases through the proper matching of a plurality of characteristic amounts, and further can inspect with a high speed, with human judgement being correspondingly provided with respect to the condition of the crease.

Also, another object of the present invention is to provide a tape crease adjusting apparatus which is capable of properly adjusting the tape creases with a high speed in accordance with the condition of the discriminated crease, as described hereinabove.

A tape crease inspecting method of the present invention inspects the crease condition of the tape by the projection of the reflection light of the stripe shaped pattern onto the tape.

Also, the tape crease inspecting apparatus of the present invention is provided with a means for projecting the reflection light of the stripe shaped patterns onto the tape, and a means of inspecting the crease condition by an analyzing operation of the pitch of the stripe shaped pattern projected onto the tape upon a plurality of inspection lines.

Also, the tape crease inspecting apparatus of the present invention is provided with a means for projecting the reflection light of the stripe shaped patterns onto the tape, a means for analyzing the pitch of the stripe shaped pattern projected onto the tape on a plurality of inspection lines so as to extract a plurality of characteristic amounts of the stripe shaped pattern, and a means for discriminating the above described tape crease condition upon which the stripe shaped pattern is projected with the use of a FUZZY reasoning method in accordance with the information of the above described plurality of characteristic amounts.

Furthermore, the tape crease adjusting apparatus of the present invention is provided with a means for adjusting the crease of the tape in accordance with the information of the condition of the discriminated crease by the use of the above described crease inspecting apparatus.

Thus, in accordance with the present invention, by the projection of the reflection light of the stripe shaped pattern onto the tape, pictures good in contrast and clear in their pattern boundaries may be provided, and also, the positioning operation of the stripe pattern is simplified.

Also, as a means is provided which analyzes the pitch of the stripe pattern projected onto the tape on a plurality of inspection lines so as to extract a plurality of characteristic amounts of the stripe patterns, the change condition of very small creases may be detected in a short time.

Also, as a means is provided of discriminating the crease condition of the stripe shaped pattern with the use of the FUZZY reasoning method in accordance with the information of a plurality of characteristic amounts, the condition changes in complicated and very small creases of a plurality of characteristic amounts may be discriminated with a high speed through the proper matching of the plurality of characteristic amounts, and also, the inspection may be effected with a high speed with human judgement being provided correspondingly with respect to the crease condition.

A means of projecting the reflection light of the stripe shaped pattern onto the tape, a means for analyzing the pitch of the stripe pattern projected onto the tape on the plurality of inspection lines so as to extract a plurality of characteristic amounts of the stripe pattern, a means for discriminating the crease condition of the stripe pattern by the use of the FUZZY reasoning method in accordance with the information of the plurality of characteristic amounts, and a means for adjusting the crease of the tape in accordance with the information of the detected crease condition are provided. The positioning of the stripe pattern is easy, and pictures which are good in contrast and clear in the boundaries of the patterns may be provided. The change condition of very small creases may be detected in a short time and a plurality of and very small crease condition changes may be discriminated by the proper matching of a plurality of characteristic amounts. High speed inspection may be effected with human judgement being correspondingly provided with the crease condition, and also the tape creases may be properly adjusted at a high speed.

BRIEF DESCRIPTION OF THE DRAWINGS

FIG. 5 is a chart illustrating how the characteristic amounts of the creases are extracted by such a tape crease inspecting apparatus as shown in FIG. 1;

DETAILED DESCRIPTION OF THE PREFERRED EMBODIMENTS

The embodiments of the present invention will be described hereinafter with reference to the drawings.

Figure 1:
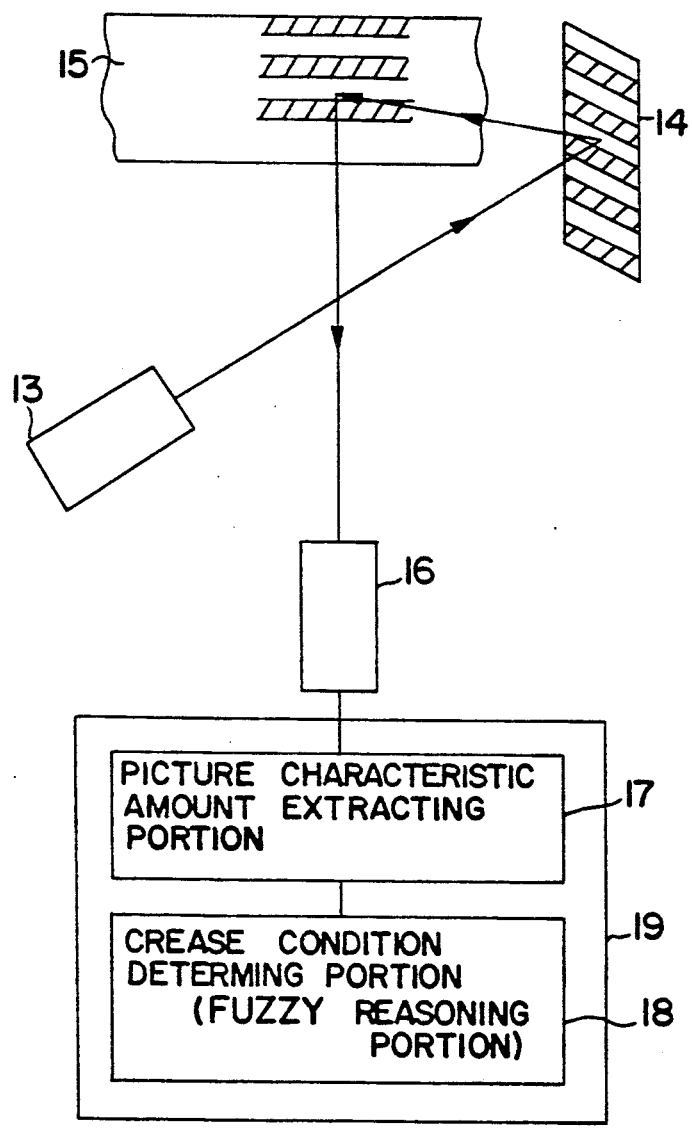
FIG. 1 is a diagram showing a schematic construction of a tape crease inspecting apparatus in a first embodiment of the present invention.

FIG. 1 is a diagram showing a summary of a tape crease inspecting apparatus in a first embodiment of the present invention. Referring to the same drawing, 13 is a projector, 14 is a reflection plate with stripe patterns printed on it, 15 is tape, 16 is an image pickup apparatus, 17 is a picture characteristic amount extracting portion, 18 is a crease condition determining portion using a FUZZY reasoning method, and 19 is a picture processing apparatus composed of the picture characteristic amount extracting portion 17 and the crease condition determining portion 18.

Figure 3:
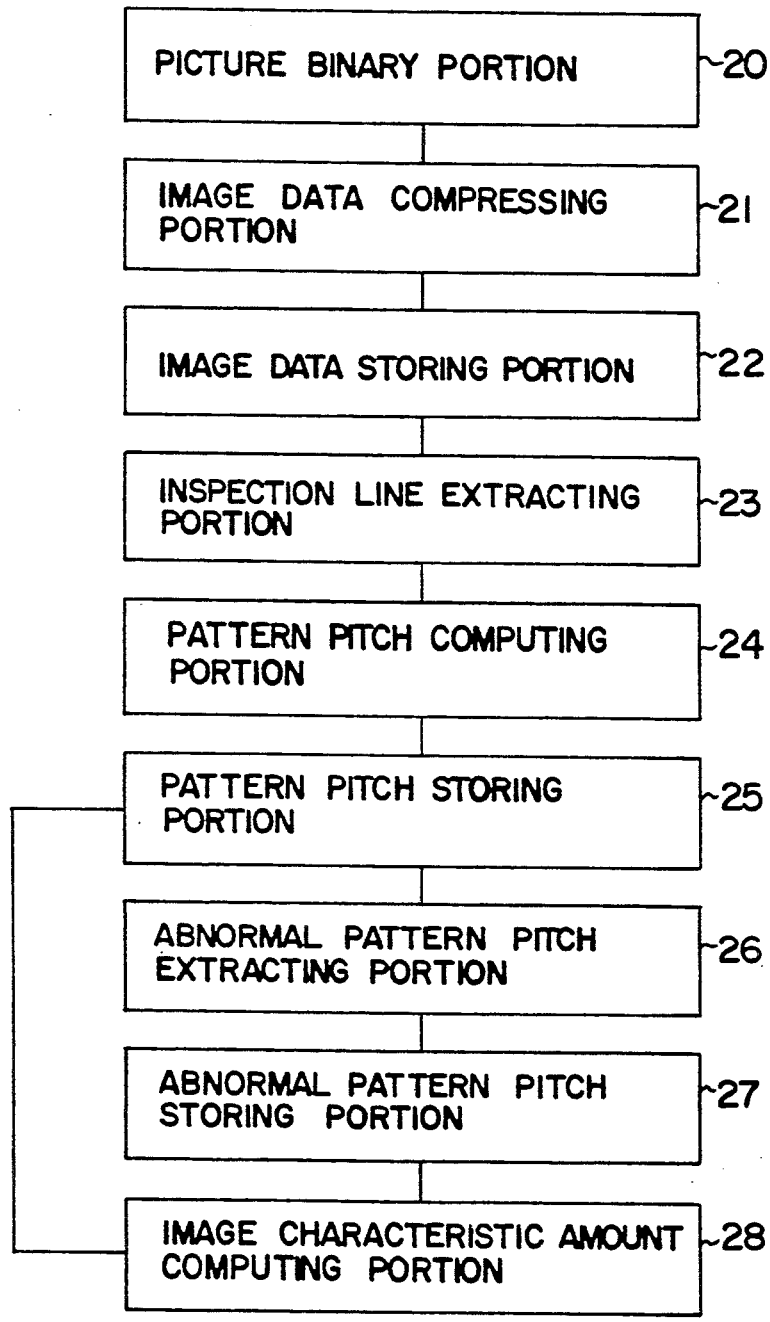
FIG. 3 is a diagram showing the construction of a picture characteristic amount extracting portion 17 in FIG. 1.

FIG. 3 is a diagram showing the construction of the picture characteristic amount extracting portion 17 in FIG. 1. Referring to the same drawing, 20 is a picture binary portion, 21 is an image data compressing portion, 22 is an image data storing portion, 23 is an inspection line extracting portion, 24 is a pattern pitch computing portion, 25 is a pattern pitch storing portion, 26 is an abnormal pattern pitch extracting portion, 27 is an abnormal pattern pitch storing portion and 28 is an image characteristic amount computing portion.

Figure 4B:
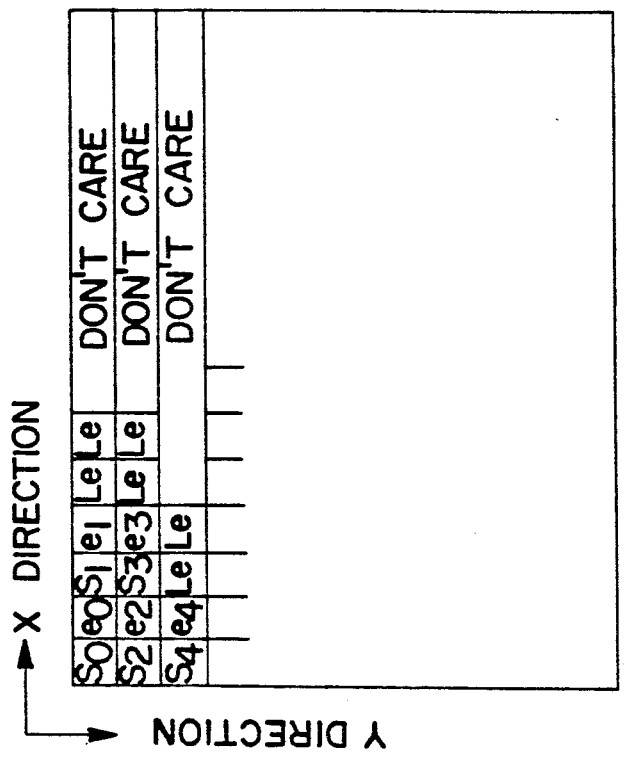
FIG. 4 is a chart showing a data construction compressed in the picture data compressing portion 21 in FIG. 3, wherein FIG. 4 (a) is a chart showing binary picture data stored in the picture memory and FIG. 4 (b) is a chart showing the compression data stored in the picture memory.
Figure 4A:
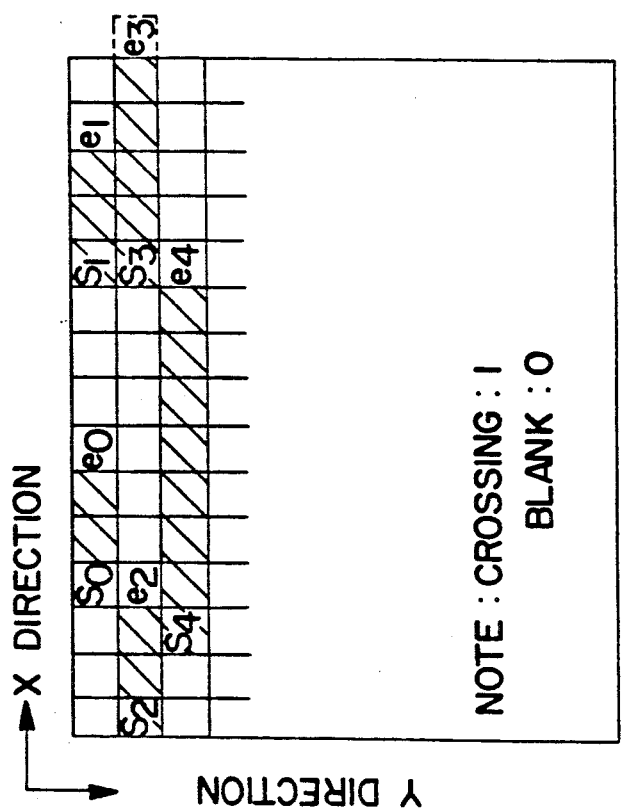

FIG. 4 is a chart showing the data construction compressed in the picture data compressing portion 21. FIG. 4 (a) shows a binary picture data stored in the picture memory, and FIG. 4 (b) shows the compressed data stored in the picture memory.

FIG. 5 is a chart illustrating how to extract the characteristic amount of a crease with the tape crease inspecting apparatus shown in FIG. 1. In the same drawing, 29 is an inspection line and 30 is the distance between stripe pattern centers on the inspection line 29 in the pattern pitch of the stripe. 31 is an abnormal pattern pitch, and 32 and 33 are the end points of the abnormal pattern pitch.

Figure 6:
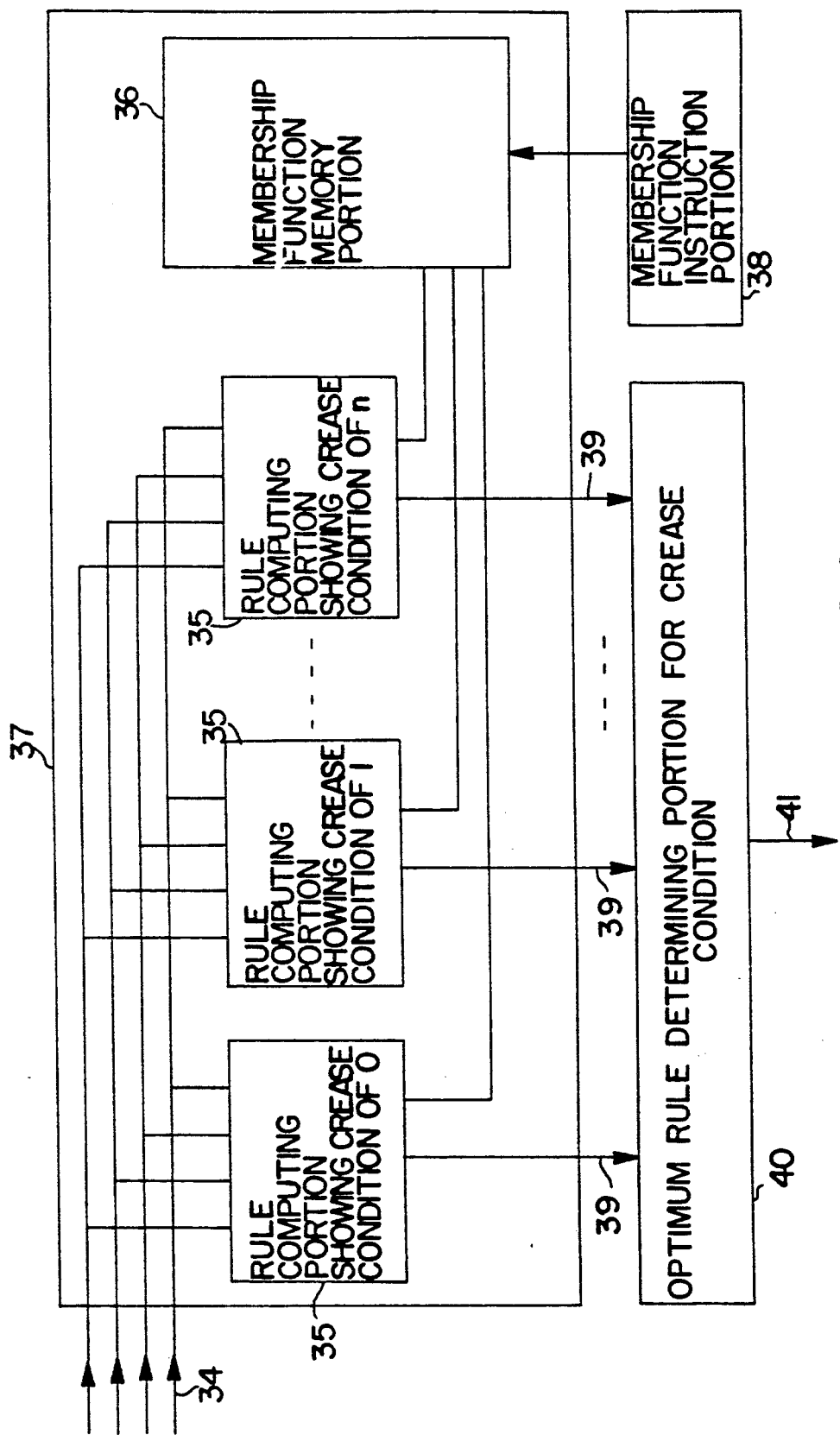
FIG. 6 is a diagram showing the construction of the crease condition determining portion 18 in FIG. 1.

FIG. 6 is a diagram showing the construction of the crease condition determining portion 18 in FIG. 1. Referring to the same drawing, 34 is a picture characteristic amount information transmission path calculated by the picture characteristic amount extracting portion 17 in FIG. 1. 35 is an inference rule computing portion corresponding to each crease condition instructed in advance. 36 is a storing portion of the membership function corresponding to the inference rule computing portion 35.

Here the membership function is an important concept in the FUZZY theory. The vagueness in the meaning of terms such as "tall", "old man" and so on can be expressed in terms of an amount. The degree to which a person who s x (cm) in height, in a range from 140 cm in height to 200 cm, is said to be tall is designated $\mu$ ($0 \leq \mu \leq 1$) being correspondingly matched to the height x. Using x for the axis of abscissae and $\mu$ for the axis of ordinates, such a graph as described in FIG. 14 may be drawn. The graph expresses the vagueness of the meaning of the term "tall" in a quantitative amount. Likewise, the vagueness of the concept of the term "old man" may be expressed by the graph of FIG. 15. The age is used as the amount of the axis of abscissae, with the axis of ordinates being the degree of oldness $\mu$.

Figure 14:
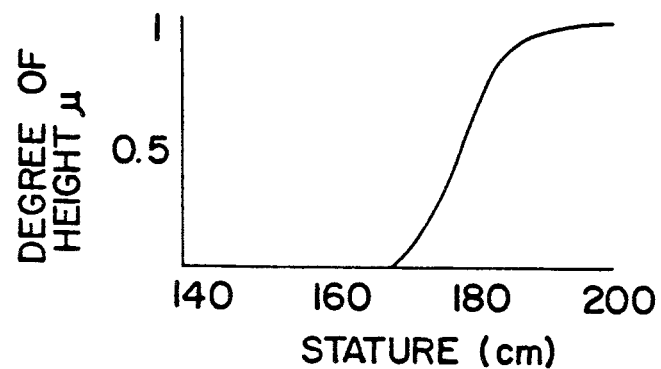
FIG. 14 and FIG. 15 are graphs illustrating the meaning of ambiguity in an amount, illustrating the concept of the membership function in the FUZZ theory.
Figure 15:
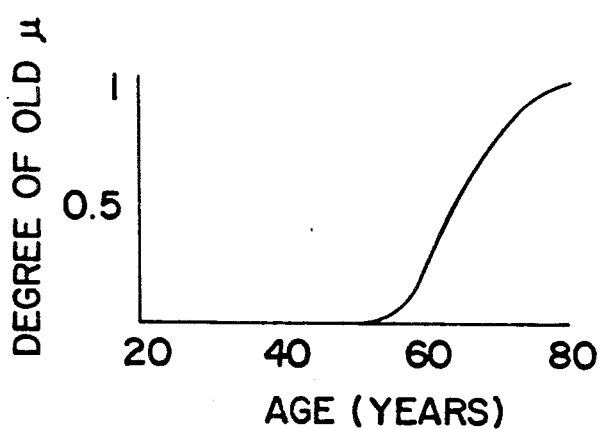

Like the graphs of FIG. 14 and FIG. 15, the function giving the degree of the meaning of a word is called the membership function in the FUZZY theory. Also, the degrees $\mu$ may be sometimes called a membership value.

37 is a rule adaptation degree computing portion composed of the inference rule computing portion 35, and a membership function memory portion 36. 38 is a membership function instruction portion. 39 is an adaptation degree information transmission path of the inference rule computed by the inference value computing portion 35. 40 is an optimum rule determining portion. 41 is a crease condition information transmission path determined by the optimum rule determining portion 40.

Figure 7:
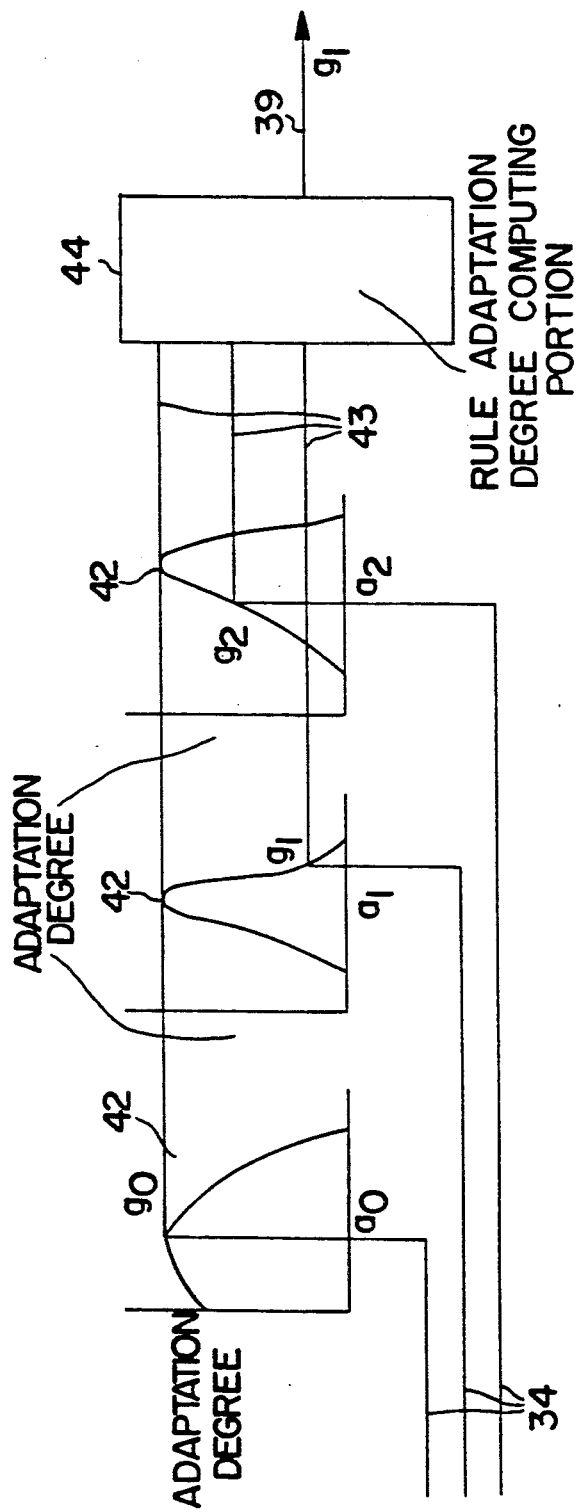
FIG. 7 is a chart illustrating how the rule adaptation degree is calculated in the inference rule computing portion of FIG. 6.

FIG. 7 is a diagram illustrating how the adaptation degree of the inference rule has been computed in the inference rule computing portion 35 of FIG. 6. In the same drawing, 42 is a membership function corresponding to the picture characteristic amount. 43 is a transmission path of the information on the membership function adaptation degree showing how much the picture characteristic amount is adapted to the membership function 42. 44 is a rule adaptation degree computing portion for determining the adaptation degree of the inference rule from the membership function adaptation degree.

Figure 8:
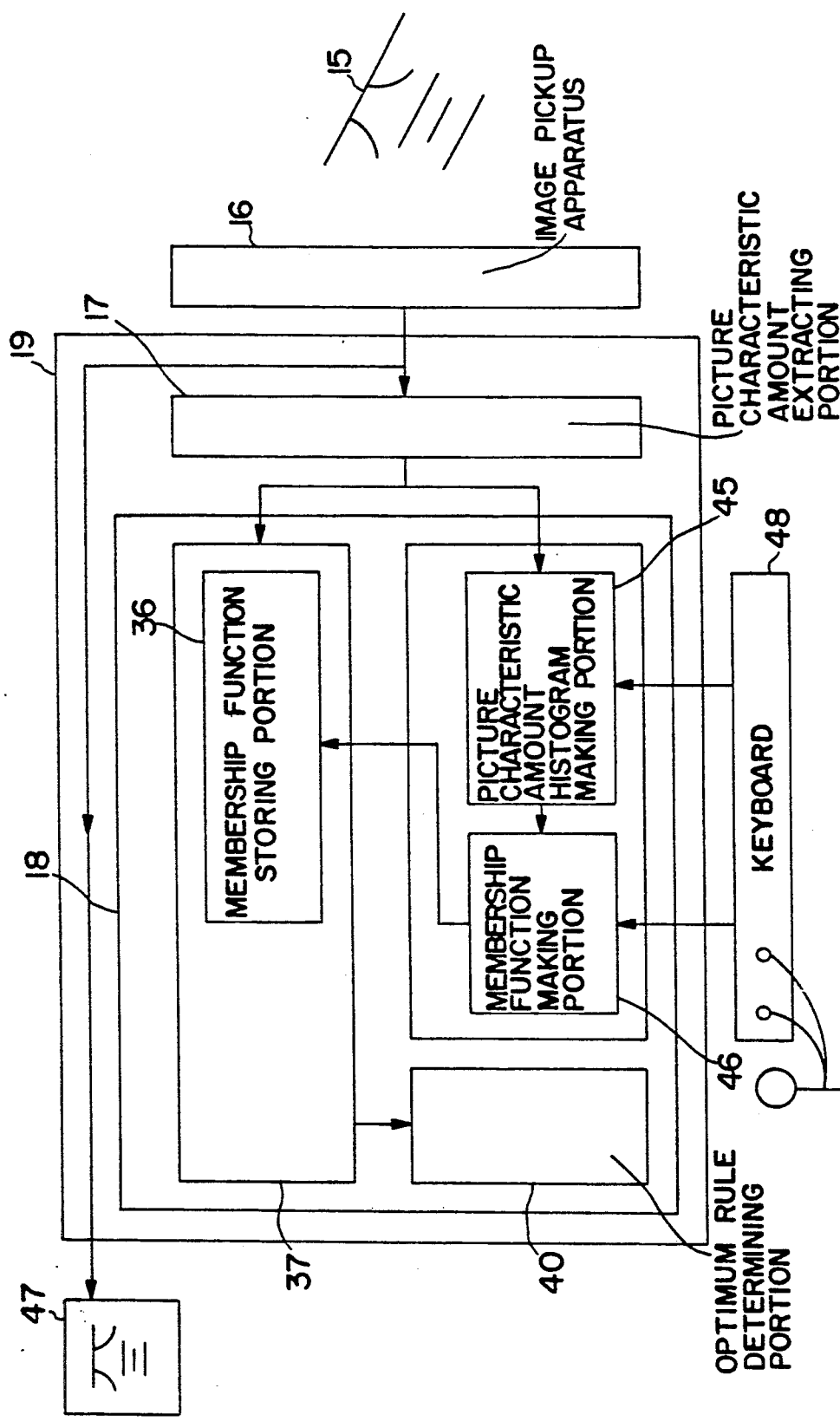
FIG. 8 is a diagram illustrating how a membership function is instructed in a membership function instruction portion of FIG. 6.

FIG. 8 is a diagram for illustrating how the membership function is instructed in the membership function instruction portion 38 of FIG. 6. In the same drawing, the like reference numerals are given to the like parts as in FIG. 1, with the illustration thereof being omitted. In the drawing, 45 is a picture characteristic amount histogram making portion. 46 is a membership function making portion. 47 is a TV monitor. 48 is a keyboard attached to the picture processing apparatus 19. 44 is a person who performs the inspection.

Figure 9A:
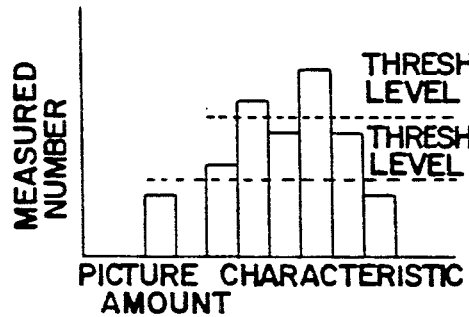
FIG. 9 is a chart showing how the picture characteristic amount histogram and a membership function are made in the picture characteristic amount histogram making portion and the membership function making portion, wherein FIG. 9 (a) is a chart showing the picture characteristic amount histogram and FIG. 9 (b) is a chart showing the membership function.
Figure 9B:
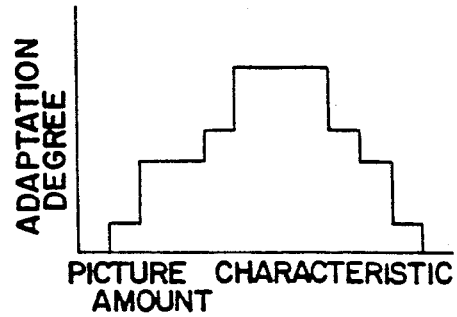

FIG. 9 is a graph showing how the picture characteristic amount histogram and the membership function are made in the picture characteristic amount histogram making portion 45 and the membership function making portion 46 of FIG. 8. FIG. 9 (a) shows the picture characteristic amount histogram and FIG. 9 (b) shows the membership function.

Figure 10:
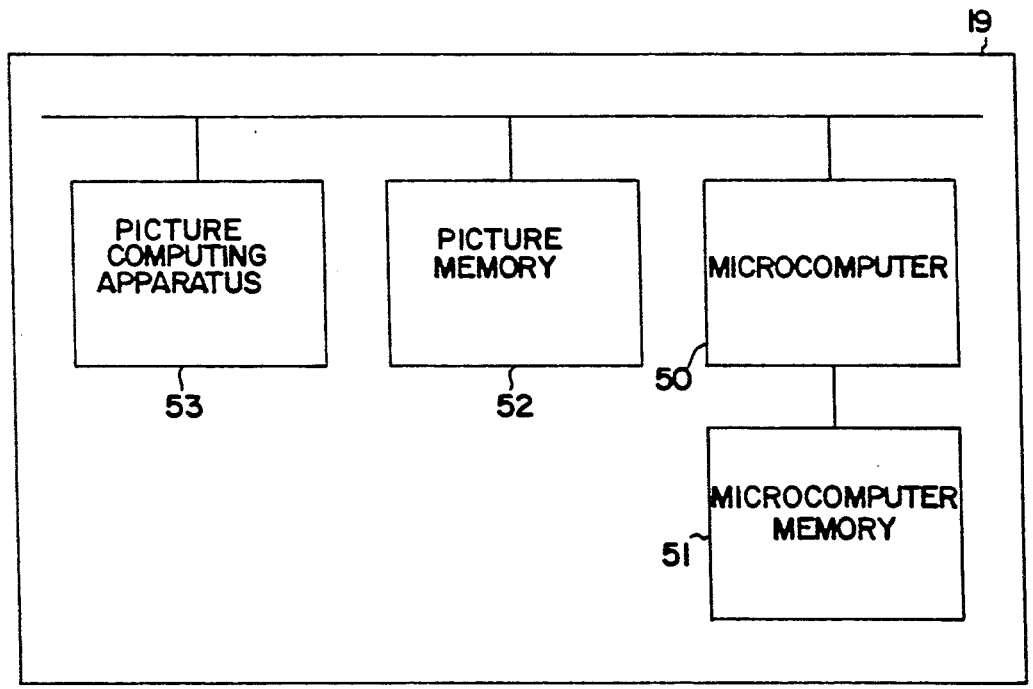
FIG. 10 is a diagram showing a construction example using a microcomputer of the picture processing apparatus 19 in FIG. 1.

FIG. 10 is a diagram showing a construction example using the microcomputer of the picture processing apparatus 19 in FIG. 1. In FIG. 10, 50 is a microcomputer, 51 is a microcomputer memory, 52 is a picture memory and 53 is a picture computing apparatus.

In the tape creasing inspecting apparatus composed as hereinabove, the operation thereof will be described below by the use of the drawings.

First, a memory of the operation will be presented. A strong light is applied upon the reflection plate 14, with the stripe shaped patterns being printed on it, from the projector 13. The light is reflected so as to project the stripe shaped patterns of the reflection plate 14 upon the tape 15. The projected light is reflected by the tape 15, and is introduced into the image pickup apparatus 16. The tape crease detection is effected by the picture processing apparatus 19 composed of the picture characteristic amount extracting portion 17 and the crease condition determining portion 18, wherein the crease condition is discriminated to effect the crease inspection.

The operation of the picture characteristic extracting portion 17 will be described hereinafter. The picture introduced by the image pickup apparatus 16 is binary-coded, compressed by the picture computing apparatus shown in FIG. 10, and stored in the picture memory 52. This is equivalent to being binary-coded, compressed by the picture computing apparatus shown in FIG. 10, and stored in the picture memory 52. This is equivalent to being binary-coded, composed by the picture binary-coding portion 20, compressed by the picture data compressing portion 21 shown in FIG. 3 and being stored in the picture data storing portion 22. Then, the pattern pitch 30 on the inspection line 29 shown in FIG. 5 is computed by the use of the microcomputer 50 from the picture data stored in the picture memory 52 to store it in the microcomputer memory 51. This is equivalent to the counting of the pattern pitch 30 on the inspection line 29 by the use of the inspection line extracting portion 23 and the pattern pitch computing portion 24 from the data stored in the picture data storing portion 22, and storing it in the pattern pitch storing portion 25. Because the compression picture data stored in the picture memory 52 is compressed in such a shape as in FIG. 4 (b), the computation cost of the pattern pitch computing portion 24 becomes smaller and high speed processing may be effected. The abnormal pattern pitch 31 is extracted by the use of the microcomputer 50 from the pattern pitch 30 stored in the microcomputer memory 51 and is itself stored in the microcomputer memory 51. This is equivalent to extracting the abnormal pattern pitch 31 by the use of the abnormal pattern pitch extracting portion 26 form the data stored in the pattern pitch storing portion 25 and storing it in the abnormal pattern pitch storing portion 27. Here the abnormal pattern pitch 31 is a pattern pitch 30 which is smaller or larger in value with respect to a certain standard value. The picture characteristic amount is calculated from the abnormal pattern pitch 31 by the use of the microcomputer 50. This is equivalent to the computing of the picture characteristic amount by the use of the picture characteristic amount computing portion 28 from the abnormal pattern pitch 31 stored in the abnormal pattern pitch storing portion 27. In the present embodiment, the number of the abnormal pattern pitches 31, the end points 32 and 33 of the abnormal pattern pitch, a gravity center coordinate of the histogram with respect to the central coordinate of the abnormal pattern pitch 31 on the coordinate axis parallel to the inspection line 29, and the number of the portion where the histogram value is 0 are provided as the picture characteristic amounts. Items except for the characteristic amount provided here may be used depending upon the condition of the crease to be caused. Although in the present embodiment the pattern pitch 30 is computed and stored in the microcomputer memory 51 by the microcomputer 50 from the compression picture data, the pattern pitch 30 may be computed by the picture computing apparatus 53 to store it in the picture memory 52. In this case, the processing speed is further improved. But in the method of computing the pattern pitch 30 with the microcomputer 50 from the compression picture data, storing it in the microcomputer memory 51, the center of the pattern may be obtained with the accuracy of ½ picture element, while in the method of computing the pattern pitch 30 with the picture computing apparatus 53 to store it in the picture memory 52, the accuracy of the pattern pitch 30 is lowered, because the accuracy of the center of the pattern is one picture element.

The operation of the crease condition determining portion (FUZZY reasoning portion) 18 will be described hereinafter. These computations are effected by the use of the microcomputer memory 51 with the microcomputer 50. The picture characteristic amount computed by the picture characteristic extracting portion 17 has plurality of respective inference rule computing portions 35 corresponding to a crease condition instructed in advance. There is an inference rule in a 1:1 relation about the pattern of the crease condition to be detected, with the inference rule computing portions 35 being provided according to the number of inference rules. The inference rule is specified by the membership function 42 shown in FIG. 7 corresponding to the picture characteristic amount. Namely, to teach the crease condition in advance is to teach the shape of the membership function 42 corresponding to the picture characteristic amount. The membership function 42 is stored in the membership function storing portion 36 in advance by the membership function instructing portion 38. In the teaching of the membership function 42, the picture with the tape 15 introduced by the image pickup apparatus 16 is displaced on the TV monitor 47 first, as shown in FIG. 8. The person 49 watches the crease condition shown on the TV monitor 47 to judge which condition this crease applies to among the crease conditions classified in advance, and inputs this crease condition into the picture processing apparatus 19 by the use of the keyboards 48. In the picture processing apparatus 19, the picture characteristic amount is kept computed by the use of the picture characteristic amount extracting portion 17 with respect to the crease shown on the TV monitor 47. In the picture characteristic amount histogram making portion 45, a picture characteristic amount histogram is made corresponding to the inference rule of the crease condition inputted by the keyboard 48 from the picture characteristic amount 34. The instruction is carried out a plurality of times to make the proper picture characteristic amount histogram. In the membership function making portion 46, smoothing and normalizing operations are effected with respect to the picture characteristic amount histogram as described in FIG. 9 (a), and a membership function of such a keystone as shown in FIG. 9 (b) is automatically made. The membership function 42 made is stored in the membership function storing portion 36. Although it is possible to approximately discriminate the crease by the sue of the membership function 42 made in this manner, a mechanism by which the person 49 can correct the membership function 42 into an optional shape by the sue of the keyboard 49 is also further provided in the present embodiment, because of cases where delicate discrimination is required and cases where unexpected creases have appeared. In the present embodiment, it is possible to effect an instruction of the membership function 42 in a proper shape with respect to the crease condition classified optionally in accordance with the senses of the person. Now, in the inference rule computing portion 3,, as shown in FIG. 7, the membership function adaptation degree showing how much the picture characteristic amount is adapted to the membership function 42 is obtained with respect to the respective picture characteristic amounts by reference of the picture characteristic amount to the respective membership functions 42 corresponding to the picture characteristic amounts. They are inputted into the rule adaptation degree computing portion 44 so a to output the adaptation degree of the inference rule with respect to the picture characteristic amount. In FIG. 7, the membership function adaptation degree is equivalent to go, g1 and g2. In the rule adaptation degree computing portion 44, a computation, with a minimum value of the membership function adaptation degree being the adaptation degree 39 of the inference rule, is effected in the present embodiment. In FIG. 7, the adaptation of the inference rule is equivalent to g1. Also, the adaptation degree of the inference rule shows how much the picture characteristic amount is applied to the instructed creases condition. In this manner, the adaptation degree of each inference rule obtained by the rule adaptation degree calculation portion 37 is inputted into the optimum rule (crease condition) determining portion 40, and the crease condition 41 is determined by the selection of the optimum rule. In the optimum rule determining portion 40 in the present embodiment, the instructed crease conditions are all considered to have the same weight and a computation is effected with the inference rule, where the adaptation degree among the adaptation degrees of the respective inference rules is a maximum value, being the optimum rule But in the present embodiment, there is an inference rule with the relation 1:1 about the pattern in the crease condition to be detected. A shape of the membership function 42 corresponding to the picture characteristic amount is instructed, but the inference rule may be set by a plurality of instructions about the pattern on the crease condition to be detected with the shape of the membership function being fixed. Also, as described hereinabove, although these computations are effected by the use of the micromemory 51 with the microcomputer 50, in order to reduce the calculation cost of the microcomputer 50 and the storing amount of the micro-memory 51, in the present embodiment, the picture characteristic amount which is the input of the membership function 42 and the adaptation degree which is the output are expressed with ten stages of dispersed integers. The membership function 42 itself is also expressed with a set of integer sequences of 10×10. Thus, the storing capacity of the micro-memory 51 may be saved and the computation is also effected mainly with the data comparison, so that a high speed computation of a few ms or lower may be effected.

By the projection of the reflection light of the stripe shaped patterns as described hereinabove, a picture which is good in contrast and clear in its pattern boundaries may be provided, so that it is possible to detect the crease condition with a simple algorithm in the detection of the crease with the use of the picture processing apparatus. Also, the stripe shaped patterns are not required to be adhered on the tape, thus simplifying the positioning operation. Also, by the analysis of the pitch of the stripe pattern projected onto the tape on a plurality of inspection lines to extract a plurality of characteristic amounts of the stripe patterns, the crease detection may be effected in accordance with the information of the crease, compressed as is necessary and sufficient, and the delicate crease change condition may be detected in a short time. Also, the condition of the crease of the stripe pattern is discriminated by the use of the FUZZY reasoning method in accordance with the information of a plurality of characteristic amounts, so complicated and delicate crease condition changes may be discriminated with high speed with a plurality of characteristic amounts being properly matched in a shape to be realized by the computer. The inspection may be effected with high speed with a person's judgement being correspondingly provided with respect to the crease condition.

Further, even in a case where the condition of the stripe shaped pattern projected onto the tape is visually inspected, discriminated directly by a worker, the effect of the inspecting method of the tape crease in the present embodiment as described hereinabove may be exhibited.

Figure 2:
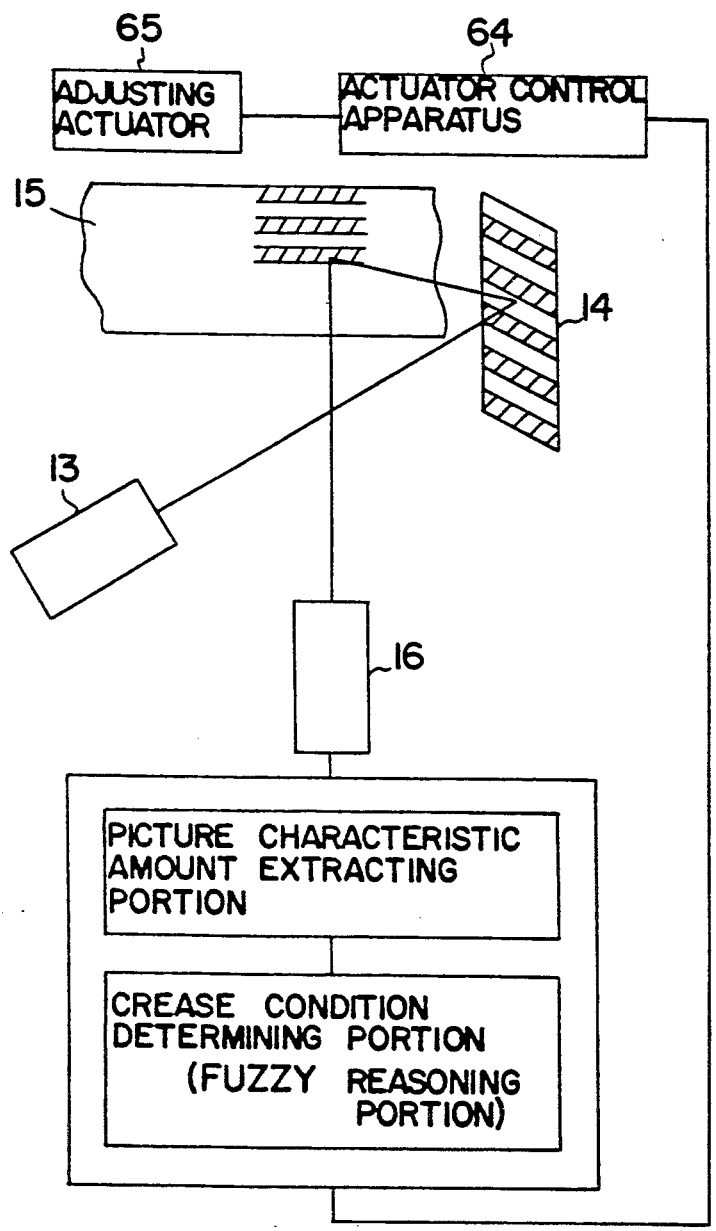
FIG. 2 is a diagram showing a schematic construction of a tape crease adjusting apparatus in a second embodiment of the present invention.

FIG. 2 is a diagram showing a summary of a second embodiment of the present invention. In the same diagram, the same numerals are given to the same parts as in FIG. 1 and the description is omitted. IN the same drawing, 64 is an actuator control apparatus and 65 is an adjusting actuator for adjusting the creases of the tape.

Figure 11:
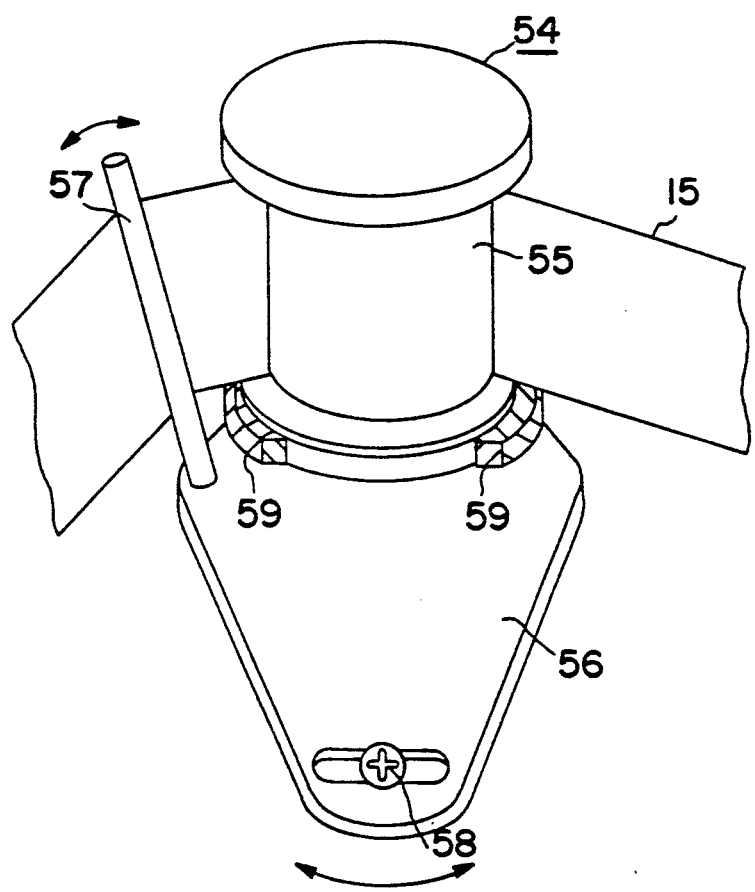
FIG. 11 is a perspective view of an essential portion near a loading post of the video tape.
Figure 12:
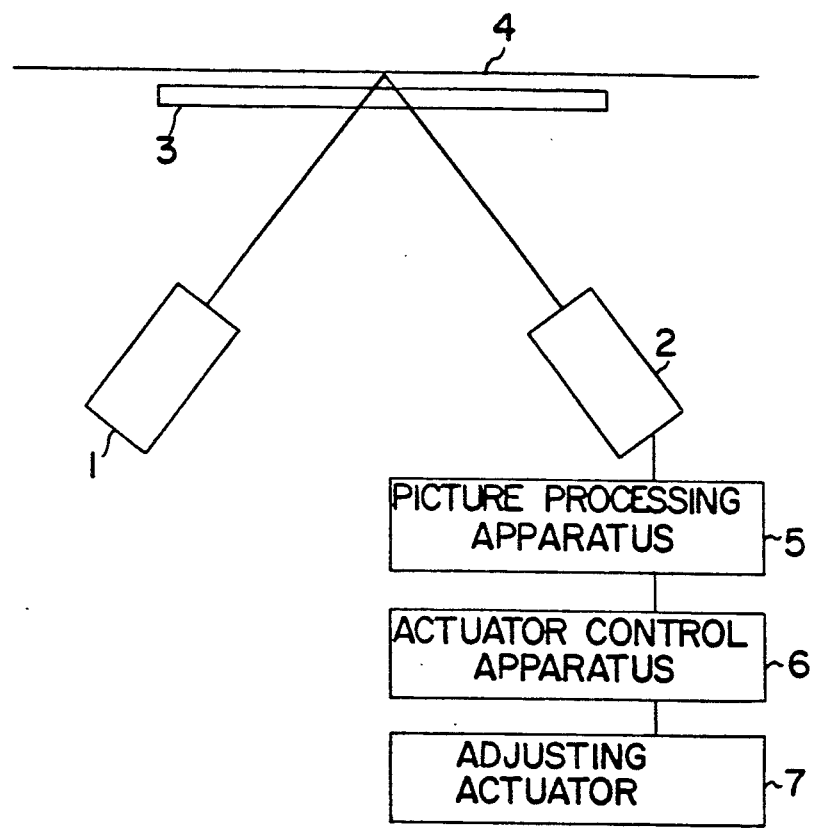
FIG. 12 is a diagram showing the construction of the tape crease inspecting and adjusting apparatus using a tape crease detecting means with conventional moire stripe processing.
Figure 13:
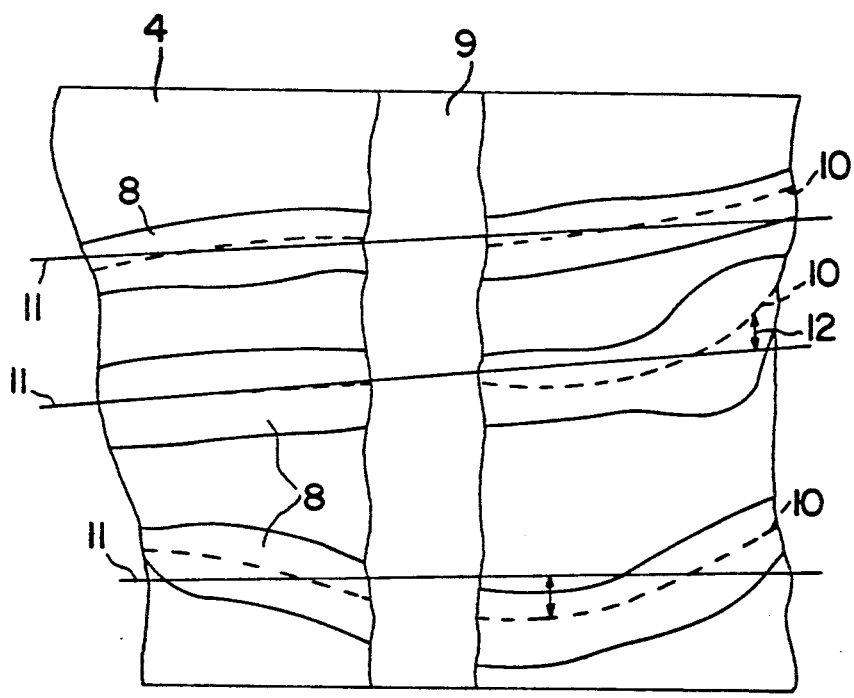
FIG. 13 shows the condition of the light projected onto the tape by the tape crease adjusting and inspection apparatus shown in FIG. 12.

FIG. 11 is a view showing a loading post and its vicinity with the video tape. In the same drawing, 54 is a loading post main body, 55 is a loading post portion, 56 is a base portion, 57 is a crease adjusting post portion, 58 is a base fixed screw and 59 is a stopper.

The adjusting apparatus for the tape crease using a tape crease inspecting apparatus composed as described hereinabove and shown in the FIG. 1 embodiment will be described hereinafter in its operation with the use of the drawings.

First, the summary of the operation will be described. As in the first embodiment, the strong light is reflected upon the reflection plate 14 with the stripe patterns printed on it from the projector 13 so as to project the stripe patterns of the reflection plate 14 onto the tape 15. The projected light is reflected by the tape 15 and is introduced into the image pickup apparatus 16. The crease detection of the tape is effected, the crease condition is discriminated, and the inspection of the crease is effected by the picture processing apparatus 19 composed of the picture characteristic amount extracting portion 17 and the crease condition determining portion 18. When the crease of the tape is not proper through the result of the inspection, the actuator control apparatus 64 moves the adjusting actuator 65 to adjust the creases. Thereafter, the inspecting adjustment is repeated until the creases becomes proper in condition.

The operation of the actuator control apparatus 64 and the adjustment actuator 65 will be described hereinafter. In FIG. 11, the loading post main body 54 is kept depressed against the stopper 59, and the base portion 56 is secured by the base fixed screw 58, thereafter if the base fixed screw 58 is loosened, the base portion 56 may be rotated to the left and the right with the contact point between the stopper 59 and the loading post main body 54 being provided as a support point. Also, as the crease adjusting post portion 57 is obliquely secured with respect to the base portion 56, the angle of the tape 15 is contact with the crease adjusting post portion 57 changes and the crease condition of the tape 15 near the loading post portion 55 changes when the base portion 56 is rotated. Namely, in order to adjust the crease condition, loosen the base fixed screw 58, rotate the base portion 56 to the left or the right, and clamp the screw after the adjustment has been completed. The actuator control apparatus 64 and the adjustment actuator 65 in the present embodiment are provided with such functions. As an interrelationship is provided between the rotation direction of the base portion 65 and causing the condition of the crease to change about the crease near the loading post of the video tape, which is the control object of the present embodiment, the actuator control apparatus 64 is provided with an adjusting mechanism which rotates the base portion 56 until the proper crease condition, with a table of adjusting rotation amounts being provided with respect to the condition of the crease detected. Also, depending upon the video deck, a difference appears in the adjustment rotation amount if the crease condition is likewise varied. Therefore, there is a case where the frequency of the adjustment is increased if the standard adjustment amount is applied, depending upon the video deck, and the time requiring the adjustment takes more time. The tape crease adjusting and inspecting apparatus of the present embodiment has information of how much the rotation amount of the base portion 5 has been made, more or less, by the comparison of the crease condition before the adjustment and after the adjustment. The actuator control apparatus 65 in the present embodiment is provided with a mechanism by which the proper adjustment amount with respect to the video deck is applied in accordance with such information.

As described hereinabove, by the adjustment of the crease of the tape in accordance with properly detected change information of a delicate crease, the crease of the tape may be properly adjusted at a high speed in accordance with the adjusting characteristic of the video deck.

According to the present invention as described hereinabove, by the projection of the reflection light of the stripe shaped patterns onto the tape pictures which are good in contrast and are clear in the boundaries of the patterns may be provided, so that the crease condition may be detected with a simple algorithm in the detecting operation of the crease by the use of the picture processing apparatus. Also, the stripe shaped pattern is not required to be adhered on the tape, and the positioning operation thereof is simplified.

Also, since a means is provided of analyzing the pitch of the projected stripe shaped pattern projected onto the tape on a plurality of inspection lines to extract a plurality of characteristic amounts of the stripe shaped pattern, the crease inspection may be effected in accordance with the information of the crease compressed with necessity and sufficiency, and the change condition of delicate creases may be detected in a short time.

Also, a means of discriminating the condition of the crease of the stripe shaped pattern by the use of the FUZZY reasoning method in accordance with the information of a plurality of characteristic amounts allows the condition change in complicated and delicate creases to be discriminated with the proper matching of a plurality of characteristic amounts in a shape to be realized by the computer. The inspection maybe effected with high speed, with a person's judgement being provided correspondingly with respect to the condition of the crease.

Also, since a means of reflecting the stripe shaped patterns with the projector to project them onto the tape, a means of analyzing the pitch of the stripe patterns projected onto the tape on a plurality of inspection lines to extract a plurality of characteristic amounts of the stripe patterns, a means of discriminating the condition of the crease of the stripe pattern with the use of the FUZZY reasoning method in accordance with the information of a plurality of characteristic amounts and a means of adjusting the crease of the tape in accordance with the information of the detected crease condition are provided, the positioning of the stripe pattern is simplified, pictures which are good in contrast and clear in the boundaries of the patterns may be provided, the change condition of delicate creases may be detected in a short time, the condition change of complicated and delicate creases maybe discriminated with high speed through the proper matching of a plurality of characteristic amounts, the inspection maybe effected with high speed with a person's judgement being correspondingly provided with respect to the condition of the crease, and also, the crease of the tape may be adjusted into the proper condition in accordance with the adjusting characteristic of the video deck.

What is claimed is:

1. A method of inspecting a tape crease, comprising:
    providing a light source and a reflection plate having a stripe shaped pattern;
    illuminating said reflection plate with said light source to cause light from said reflection plate to be reflected onto the tape in the stripe shaped pattern; and
    inspecting the striped shaped pattern reflected onto the tape.

2. The method of claim 1, wherein said step of inspecting comprises:
    providing an image pickup apparatus and a picture processing apparatus;
    picking up the image of the stripe shaped pattern reflected on the tape with said image pickup apparatus;
    introducing the image to said picture processing apparatus; and
    processing the image with said picture processing apparatus.

3. The method of claim 2, wherein:
    said picture processing apparatus comprises a picture characteristic amount extracting portion; and
    said step of processing comprises extracting a picture characteristic amount with said picture characteristic amount extracting portion by:
      binary-coding the image into binary-coded image data, compressing the image data and storing the compressed image data,
      computing a pattern pitch on an inspection line of the stripe shaped pattern from the image data and storing the pattern pitch of the inspection line,
      extracting an abnormal pattern pitch from the stored pattern pitch and storing the abnormal pattern pitch, wherein the abnormal pattern pitch is smaller or larger than a standard value, and
      calculating a picture characteristic amount from the abnormal pattern pitch.

4. The method of claim 3, wherein:
    said picture processing apparatus further comprises a crease condition determining portion; and
    said step of processing further comprises determining a crease condition with said crease condition determining portion by:
      inputting a crease condition,
      making a picture characteristic amount histogram corresponding to an inference rule of the inputted crease condition,
      smoothing and normalizing the histogram to make a membership function, and
      obtaining a membership function adaptation degree for the picture characteristic amount by referring the picture characteristic amount to the membership function.

5. The method of claim 1, wherein said step of inspecting comprises computing a pattern pitch along inspection lines of the stripe shaped pattern, extracting an abnormal pattern pitch from the pattern pitch and calculating a picture characteristic amount from the abnormal pattern pitch.

6. A tape crease inspecting apparatus, comprising:
    means for projecting light and reflecting the light onto a tape in a stripe shaped pattern; and
    a means for inspecting the stripe shaped pattern reflected onto the tape on a plurality of inspection lines and determining the pitch of the stripe shaped pattern on the plurality of inspection lines, and for analyzing the pitch of the stripe shaped pattern reflected onto the tape on the plurality of inspection lines.

7. The tape crease inspecting apparatus of claim 6, wherein said means for projecting and reflecting light comprises a projector and a reflection plate having stripe shaped patterns thereon.

8. The tape crease inspecting apparatus of claim 6, wherein said means for inspecting and analyzing comprises an image pickup apparatus and a picture processing apparatus.

9. The tape crease inspecting apparatus of claim 8, wherein said picture processing apparatus includes means for binary-coding an image into binary-coded image data, compressing the image data and storing the compressed image data, computing the pattern pitch on the inspection lines of the stripe shaped pattern from the image data and storing the pattern pitch of the inspection lines, extracting an abnormal pattern pitch from the stored pattern pitch and storing the abnormal pattern pitch, wherein the abnormal pattern pitch is smaller or larger than a standard value, and calculating a picture characteristic amount from the abnormal pattern pitch.

10. The tape crease inspecting apparatus of claim 9, wherein said picture processing apparatus further includes means for inputting a crease condition, making a picture characteristic amount histogram corresponding to an inference rule of the inputted crease condition, smoothing and normalizing the histogram to make a membership function, and obtaining a membership function adaptation degree for the picture characteristic amount by referring the picture characteristic amount to the membership function.

11. The tape crease inspecting apparatus of claim 8, wherein said picture processing apparatus comprises at least a picture computing apparatus and a picture memory operatively connected to each other.

12. The tape crease inspecting apparatus of claim 11, wherein said picture processing apparatus further comprises a microcomputer operatively connected with said picture computing apparatus and said picture memory, and a microcomputer memory.

13. The tape crease inspecting apparatus of claim 8, wherein said picture processing apparatus comprises:
 a picture characteristic amount extracting portion operatively connected to with said image pickup apparatus; and
 a crease condition determining portion connected to said picture characteristic amount extracting portion, said crease condition determining portion having a rule adaptation degree computing portion connected with said picture characteristic amount extracting portion, a membership function making portion connected with said rule adaptation degree computing portion, a picture characteristic amount histogram making portion connected with said picture characteristic amount extracting portion and said membership function making portion, and an optimum rule determining portion connected with said rule adaptation degree computing portion.

14. The tape crease inspecting apparatus of claim 13, wherein said rule adaptation degree computing portion comprises an inference rule computing portion and a membership function memory portion.

15. The tape crease inspecting apparatus of claim 13, and further comprising a keyboard connected to said membership function making portion and said picture characteristic amount histogram making portion and a TV monitor connected to said image pickup apparatus.

16. A tape crease inspecting apparatus, comprising:
 a means for projecting light and reflecting the light onto a tape in a stripe shaped pattern;
 a means for analyzing the pitch of the stripe shaped pattern reflected onto the tape on a plurality of inspection lines and extract from the pitch of the stripe shaped pattern a plurality of characteristic amounts of the stripe shaped pattern; and
 a means for discriminating a condition of a crease of the tape onto which the stripe shaped pattern is reflected using fuzzy logic and the plurality of characteristic amounts extracted by said means for analyzing.

17. The tape crease inspecting apparatus of claim 16, and further comprising a means for adjusting the crease of the tape in response to the discriminated condition of the crease of the tape.

18. The tape crease inspecting apparatus of claim 17, wherein said means for adjusting the crease of the tape comprises an actuator control apparatus and an adjusting actuator.

* * * * *